(12) United States Patent
Mathieu

(10) Patent No.: US 8,294,764 B2
(45) Date of Patent: Oct. 23, 2012

(54) EXTENDED DEPTH-OF-FIELD SURVEILLANCE IMAGING SYSTEM

(76) Inventor: Gilles Mathieu, Kennedy Town (HK)

( * ) Notice: Subject to any disclaimer, the term of this patent is extended or adjusted under 35 U.S.C. 154(b) by 424 days.

(21) Appl. No.: 12/660,202

(22) Filed: Feb. 23, 2010

(65) Prior Publication Data

US 2010/0225759 A1 Sep. 9, 2010

(30) Foreign Application Priority Data

Mar. 9, 2009 (EP) .................................. 09305212

(51) Int. Cl.
*H04N 7/18* (2006.01)
*G06K 9/34* (2006.01)
*G02B 15/14* (2006.01)

(52) U.S. Cl. ................ 348/143; 348/E07.085; 359/365; 359/676; 359/691

(58) Field of Classification Search .................... None
See application file for complete search history.

(56) References Cited

U.S. PATENT DOCUMENTS

| | | | |
|---|---|---|---|
| 4,124,276 A | 11/1978 | Okano | |
| 4,898,461 A | 2/1990 | Portney | |
| 5,485,314 A * | 1/1996 | Sato | 359/691 |
| 5,633,757 A * | 5/1997 | Park | 359/650 |
| 5,748,371 A | 5/1998 | Cathey et al. | |
| 6,927,922 B2 | 8/2005 | George et al. | |
| 6,940,649 B2 | 9/2005 | Dowsky | |
| 7,002,755 B2 * | 2/2006 | Mihara et al. | 359/680 |
| 7,061,693 B2 | 6/2006 | Zalevski | |
| 7,158,317 B2 | 1/2007 | Ben-Eliezer et al. | |
| 7,209,293 B2 | 4/2007 | Gaida et al. | |
| 7,215,493 B2 | 5/2007 | Olmstead et al. | |
| 7,218,448 B1 | 5/2007 | Cathey et al. | |
| 7,224,540 B2 | 5/2007 | Olmstead et al. | |
| 7,260,251 B2 | 8/2007 | Dowsky | |
| 7,336,430 B2 | 2/2008 | George et al. | |
| 7,365,917 B2 | 4/2008 | Zalevsky | |

(Continued)

FOREIGN PATENT DOCUMENTS

EP 1 978 394 A1 10/2008

(Continued)

OTHER PUBLICATIONS

Mouroulis, P., "Depth of field extension with spherical optics," Opt. Exp., vol. 16, No. 17, Aug. 18, 2008.

*Primary Examiner* — Ranodhi Serrao
*Assistant Examiner* — Thomas Richardson
(74) *Attorney, Agent, or Firm* — Opticus IP Law PLLC

(57) ABSTRACT

An extended depth-of-field (EDOF) surveillance imaging system (8) that has a lens system (10) with a total lens power $\phi_T$ and an amount of spherical aberration SA where $0.2\lambda \leq SA \leq 2\lambda$. The lens system includes first lens group (G1) and a second lens group (G2). The first lens group has first and second confronting meniscus lens elements (L1, L2) that have an overall optical power $\phi_1$ such that $|\phi_1/\phi_T| \leq 0.05$. The second lens group has a doublet (D1) and a most imagewise positive lens element (L5). An aperture stop (AS) is arranged either between the first and second lens groups or within the second lens group. An image sensor (30) is arranged to receive the image and form therefrom a digitized electronic raw image. An image processor receives and digitally filters the digitized electronic raw image to form a digitized contrast-enhanced image.

15 Claims, 17 Drawing Sheets

U.S. PATENT DOCUMENTS

| | | |
|---|---|---|
| 7,469,202 B2 | 12/2008 | Dowsky et al. |
| 7,667,900 B2 * | 2/2010 | Muratani ............... 359/691 |
| 2003/0210471 A1 * | 11/2003 | Mihara et al. .............. 359/691 |
| 2004/0174578 A1 * | 9/2004 | Hoogland et al. ............ 359/12 |
| 2006/0050409 A1 | 3/2006 | George et al. |
| 2006/0164736 A1 | 7/2006 | Olmstead et al. |
| 2006/0171041 A1 | 8/2006 | Olmstead et al. |
| 2007/0236573 A1 | 10/2007 | Alon |
| 2007/0247725 A1 | 10/2007 | Dowsky |
| 2008/0151391 A1 | 6/2008 | Zalevsky |
| 2010/0194853 A1 * | 8/2010 | Matsusaka et al. ........... 348/36 |
| 2010/0328517 A1 * | 12/2010 | Mathieu ................ 348/340 |

FOREIGN PATENT DOCUMENTS

WO    WO 2008/122888    10/2008

* cited by examiner

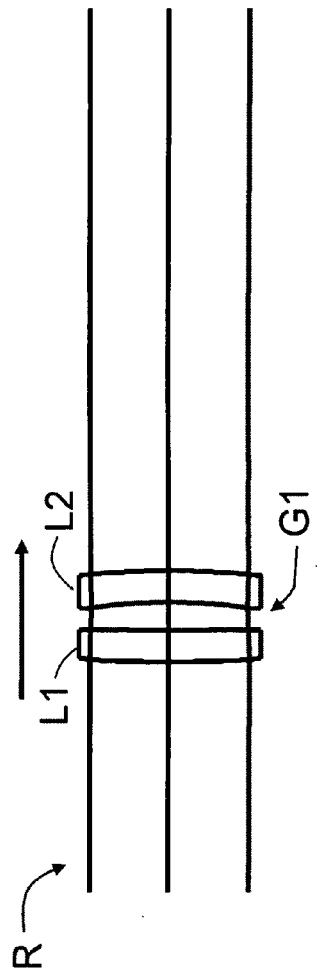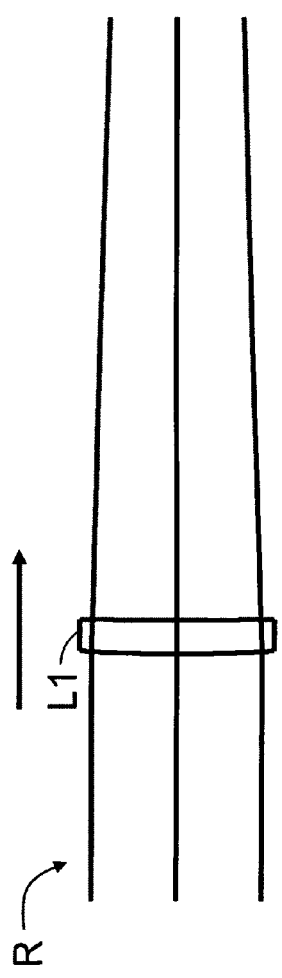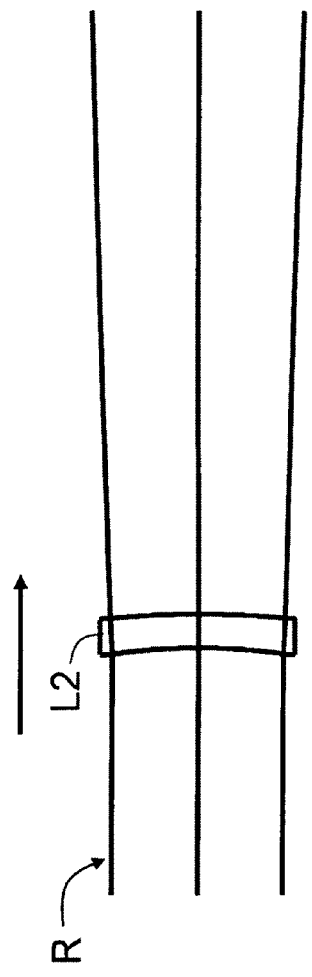

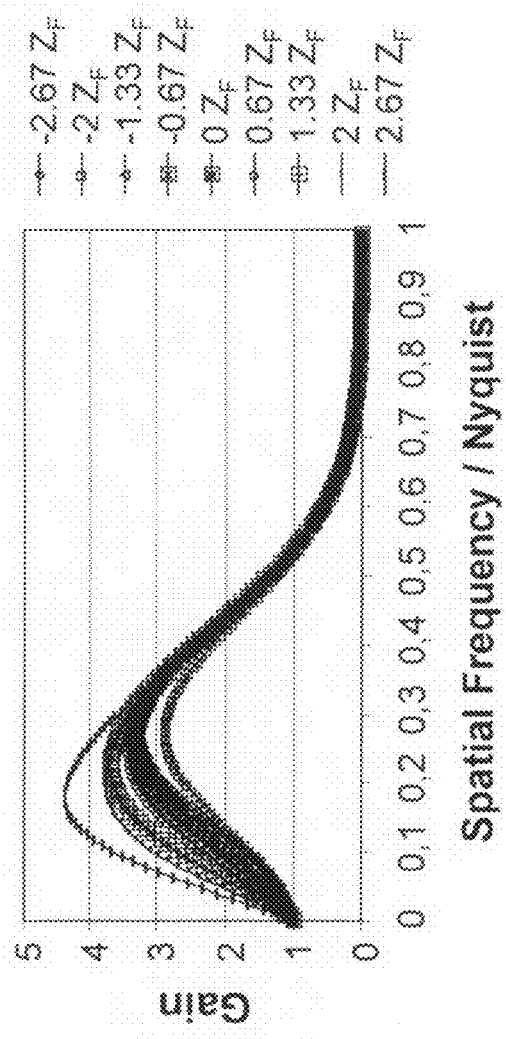
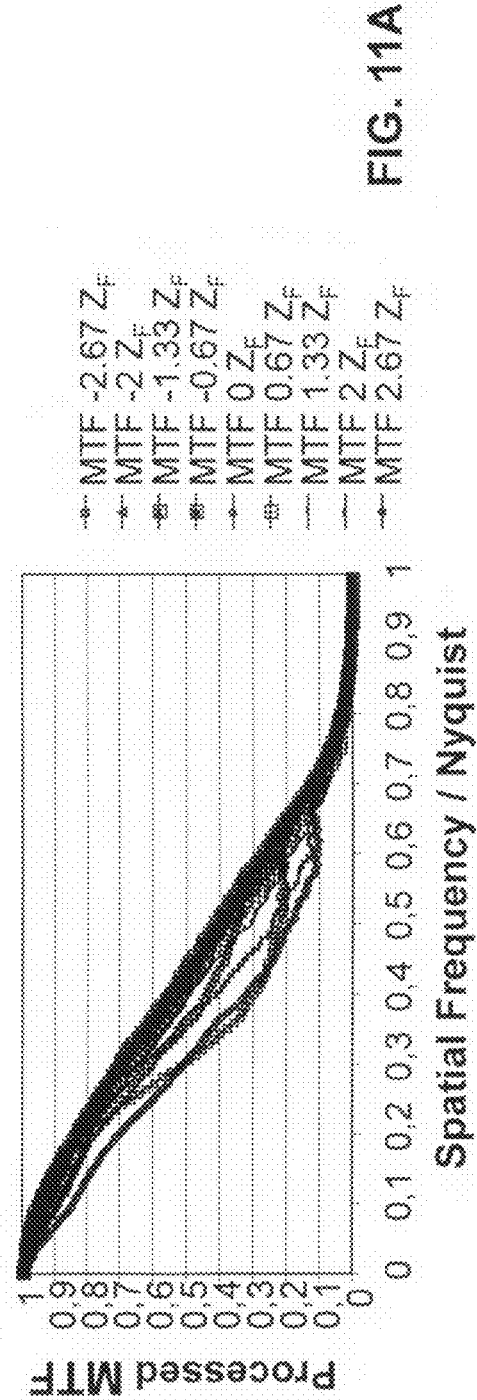
FIG. 10A
FIG. 11A

US 8,294,764 B2

EXTENDED DEPTH-OF-FIELD SURVEILLANCE IMAGING SYSTEM

CLAIM OF PRIORITY

This Application claims priority under 35 U.S.C. §119 from European Patent Application Serial No. EP09305212, filed on Mar. 9, 2009, which Application is incorporated by reference herein.

FIELD OF THE INVENTION

The present invention relates generally to surveillance imaging systems, and in particular to such imaging systems having an extended depth-of-field.

BACKGROUND ART

Extended depth-of-field ("EDOF") imaging systems (also referred to as "extended depth-of-focus" imaging systems) have seen increased use in various imaging applications such as biometrics (e.g., iris recognition), bar-code scanners, closed-circuit television (CCTV) systems, and other types of surveillance systems.

The optical (lens) systems of EDOF imaging systems typically include a non-circularly symmetric "wavefront coding" plate arranged in the entrance pupil to impart a complex wavefront shape.

Since EDOF imaging systems are desirable for use in an increasingly greater number of imaging applications, there is a need for EDOF imaging systems that use conventional rotationally symmetric lens elements but that can still provide EDOF imaging capability for a wide range of applications, including surveillance applications.

SUMMARY OF THE INVENTION

An aspect of the invention is an EDOF imaging system for forming an image of an object over an EDOF at an imaging wavelength $\lambda$. The EDOF imaging system includes a lens system having first and second lens groups. The most objectwise first lens group includes two confronting meniscus lens elements configured so that the first lens group has substantially no optical power (i.e., 5% or less of the total lens system power) but that serves to correct aberrations (i.e., provide wavefront correction).

The lens system also includes an imagewise second lens group consisting of three lens elements, two of which form a doublet. The second lens group is configured so that it contains substantially all of the optical power in the lens system (i.e., 95% or more of the total lens system power) and thus serves to form the image of the object. Aperture stop AS is located either in between the first and second lens groups G1 and G2 or within the second lens group.

The lens system is configured to have an amount SA of spherical aberration (hereinafter, "spherical aberration SA") that provides the EDOF capability. In example embodiment, spherical aberration SA is selected such that $0.2\lambda \leq SA \leq 2\lambda$, or more preferably $0.5\lambda \leq SA \leq 1\lambda$ or even more preferably $SA = 0.75\lambda$.

The EDOF imaging system further includes an image sensor that provides a raw digitized image of the object. This raw image can be used directly for select imaging applications. For other applications, the EDOF imaging system includes an image processor operably coupled to the image sensor and configured to receive and process the raw digitized image using an enhanced modulation transfer function to form an enhanced digitized image, i.e., an image having acceptable image contrast over a DOF larger than the corresponding diffraction-limited DOF.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

BRIEF DESCRIPTION OF THE DRAWINGS

FIG. 2A is a schematic diagram of the first lens group of the lens system of the EDOF imaging system of FIG. 1, and illustrates the minimal change in the paths of the light rays passing therethrough due to the substantially afocal nature and weak optical power of the first lens group;

FIG. 2B shows light rays passing through just the first lens element (lens L1) of an example first lens group, and illustrates the relatively weak positive optical power of this most objectwise lens element;

FIG. 2C shows light rays passing through just the second lens element (lens L2) of the example first lens group, and illustrates the relatively weak negative optical power of this lens element;

FIG. 10A is a plot of the gain function of the spatial frequency accordingly to the known defocus distance;

FIG. 11A is the plot of the enhanced MTF produced by the multiplication of the raw MTF on FIG. 9 by the gain function on FIG. 10A at various defocused distances;

Figure 1:
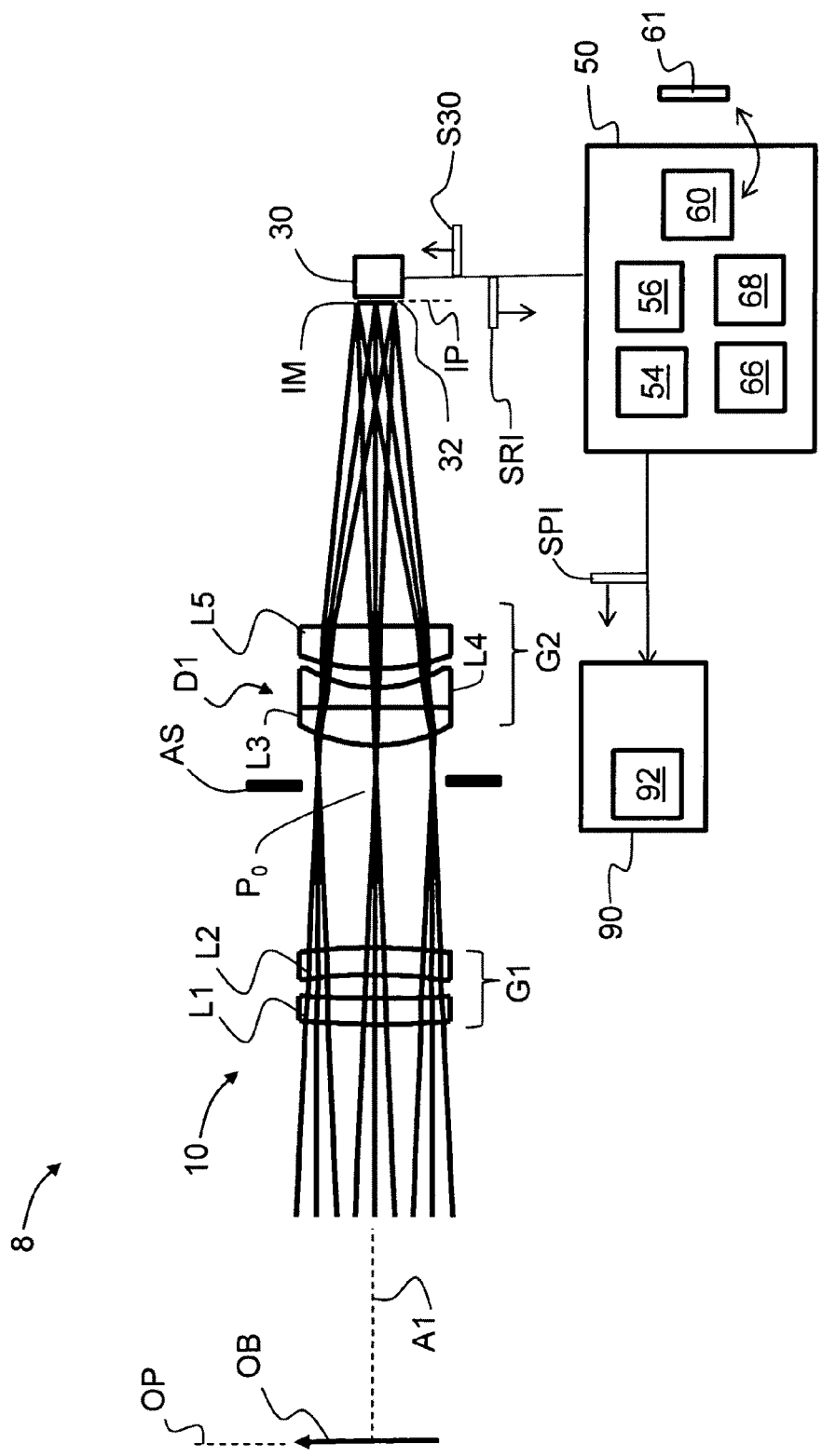
FIG. 1 is a schematic diagram of an example embodiment of the EDOF imaging system according to the present invention.

The various elements depicted in the drawing are merely representational and are not necessarily drawn to scale. Certain sections thereof may be exaggerated, while others may be minimized. The drawing is intended to illustrate an example embodiment of the invention that can be understood and appropriately carried out by those of ordinary skill in the art.

DETAILED DESCRIPTION OF THE INVENTION

The present invention relates generally to surveillance imaging systems, and in particular to such imaging systems having an extended depth-of-field. Example applications for the EDOF imaging system described herein include closed-circuit cable television (CCTV), general surveillance such as remote image identification (e.g., license plate reading), and telephoto still cameras.

Since the depth of field DOF and the depth of focus DOF' are related by the axial magnification $M_A$ and lateral magnification $M_L$ of lens system 10 (introduced and discussed below) via the relationships DOF'=$(M_A)$ DOF=$(M_L)^2$ DOF, lens system 10 is said to have an "extended depth of field" (EDOF) for the sake of convenience. One skilled in the art will recognize that this expression also implies that lens system 10 has a corresponding "extended depth of focus" as well. Thus, either the extended depth of field EDOF or the extended depth of focus EDOF' is referred to below, depending on the context of the discussion.

FIG. 1 is a schematic diagram of an example embodiment of an EDOF imaging system 8 of the present invention. EDOF imaging system 8 includes a lens system 10 for forming an image IM in an image plane IP of an object OB in an object plane OP. Lens system 10 has an optical axis A1 along which is arranged a most objectwise first lens group G1 and a most imagewise second lens group G2. First lens group G1 includes first and second meniscus lens elements L1 and L2 with respective surfaces S1, S2 and S3 and S4 (see FIG. 3). The most objectwise first meniscus lens element L1 has surfaces S1 and S2 that are concave with respect to the image plane, while the most imagewise second meniscus lens element L2 has surfaces S3 and S4 that are concave with respect to the object plane. Thus, the two meniscus lenses are positioned in a confronting configuration.

The optical power $\phi_1$ of first (front) lens group G1 is small compared to the power $\phi_2$ of the second (rear) lens group G2. Thus, the first lens group G1 is almost an afocal system. The main function of first lens group G1 is to control the wavefront quality across the image field rather than to contribute substantial power for imaging object OB.

In the Example described below, the focal length F1 of lens group G1 as produced by the two meniscus lens elements L1 and L2 is F1=−57 meters (m) and represents only 0.15% of the power of second lens group G2, which has a focal length F2=86 mm. Thus, in an example embodiment, the range of optical power of first lens group G1 represents less than 5% of the total optical power $\phi_T$ for EDOF lens system 10—i.e., $|\phi_1/\phi_T| \leq 0.05$.

The allocation of power between meniscus lenses L1 and L2 is illustrated in FIGS. 2A through 2C. FIG. 2A is a schematic diagram of an example lens group G1 and illustrates the minimal change in the paths of the light rays R passing therethrough. FIG. 2B illustrates lens L1 alone and illustrates the relatively weak positive optical power of this most objectwise lens element, which in this example has a focal length of $f_1$=478 mm. FIG. 2C illustrates lens L2 alone and illustrates the relatively weak negative optical power of this example lens element, which has a focal length of $f_2$=−470 mm (note that optical power $\phi$=1/f).

In some example embodiments, meniscus lens L1 has positive power, and meniscus lens L2 has negative power, while in other example embodiments meniscus lens L1 has negative power, and meniscus lens L2 has positive power. Lens group G1 can thus have a small amount of optical power, and this small amount can be either negative or positive as compared to the total power of the lens system. The overall optical power $\phi_1$ of lens group G1 can also be equal to or nearly equal to zero.

With reference again to FIG. 1, second lens group G2 has three lens elements L3, L4 and L5, with lens elements L3 and L4 constituting a doublet D1. Second lens group G2 contains substantially all if not all of the optical power in EDOF lens system 10 and thus plays the main role in forming image IM of object OB. An aperture stop AS is located either in between the first and second lens groups G1 and G2 or within lens group G2. Doublet D1 with lenses L3 and L4 has surfaces S5, S6 (which is an internal surface) and S7, and lens L5 has surfaces S8, S9. In an example embodiment, lens L3 has positive power, lens L4 has negative power, and lens L5 has positive power.

The surface curvatures of lenses L1 and L2 in lens group G1 allow for adjusting the spherical aberration SA while keeping control of the field aberrations generated by lens group G2. Setting a select amount of spherical aberration SA can also be accomplished by selecting one or more surface curvatures of doublet D1. In an example embodiment, one or more of lenses L1 through L5 are made of either glass or plastic.

In one embodiment, lens system 10 is corrected over a spectral range of 400 nm-2500 nm, i.e., includes visible and near infrared. This allows lens system 10 to support both daylight and infrared illumination without requiring a change in the focus setting.

Lens system 10 is designed to have efficient correction of field aberrations such as coma and astigmatism. The field curvature is controlled by appropriately selecting the index of refraction of the negative lens element L4 in doublet D1. Lens system 10 has an overall focal length FL and is also configured to image in the range from an infinite distance to a distance of about 10·FL.

The Role of Spherical Aberration

Figure 3:
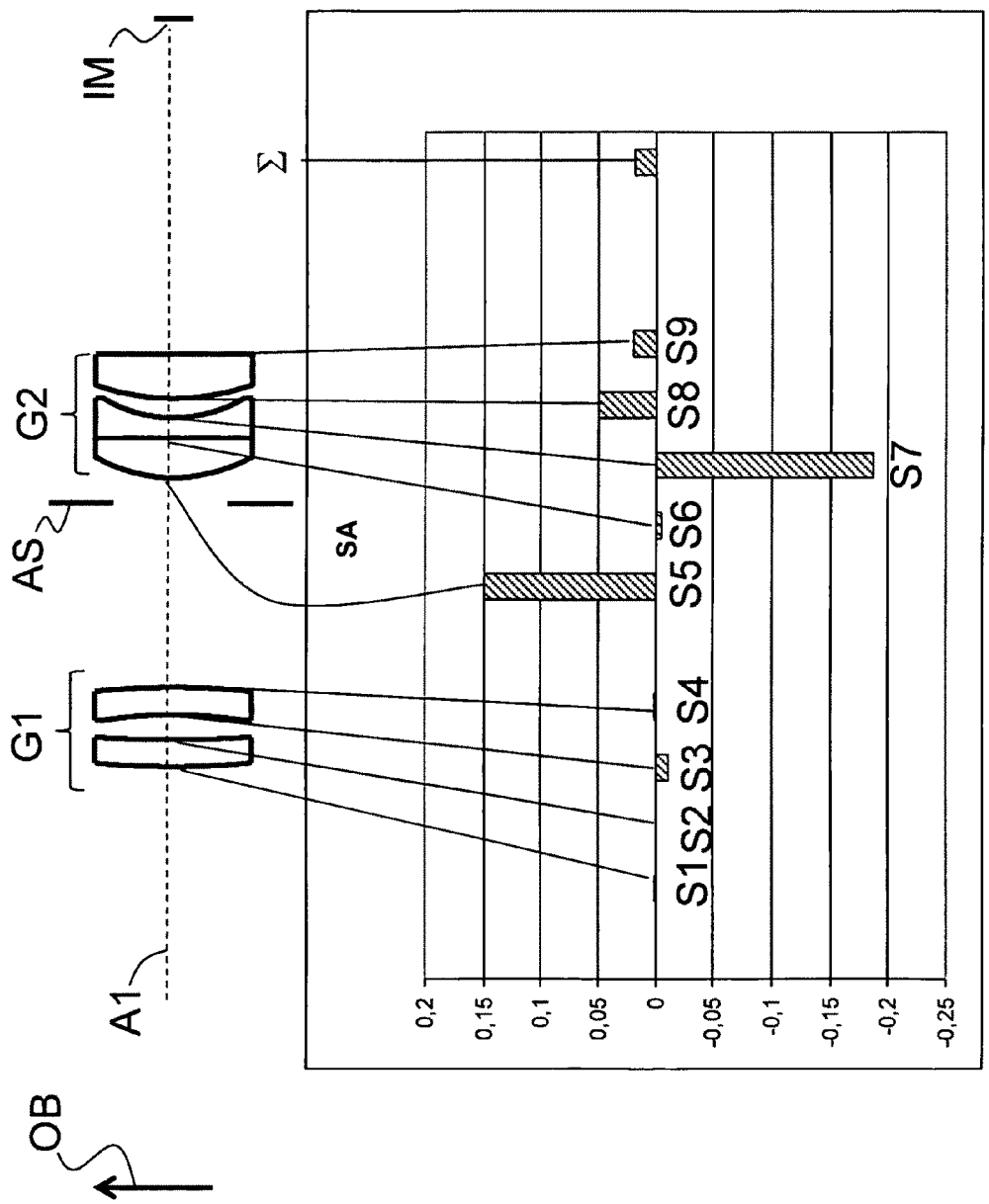
FIG. 3 is a schematic diagram of the amount of spherical aberration SA contributed by each surface of an example lens system, along with the total amount ("sum") as indicated by $\Sigma$.

Lens system 10 is designed to have the aforementioned amounts of spherical aberration so that the DOF is increased as compared to that of the corresponding diffraction limited lens. FIG. 3 is a schematic diagram of the amount of spherical aberration SA contributed by each surface of an example EDOF lens system 10, along with the total amount ("sum") as indicated by Σ.

The main control of spherical aberration SA is provided by surfaces S5 and S7 of doublet D1, which produces two opposite values of spherical aberration SA. The negative contribution from the most imagewise surface S7 of lens L4 has more weight to compensate partially for the positive contribution from the most objectwise surface S5 of lens L3. The sum Σ of the spherical aberration SA (based on first Seidel aberration terms) for lens system 10 is about +0.2λ.

Figure 4:
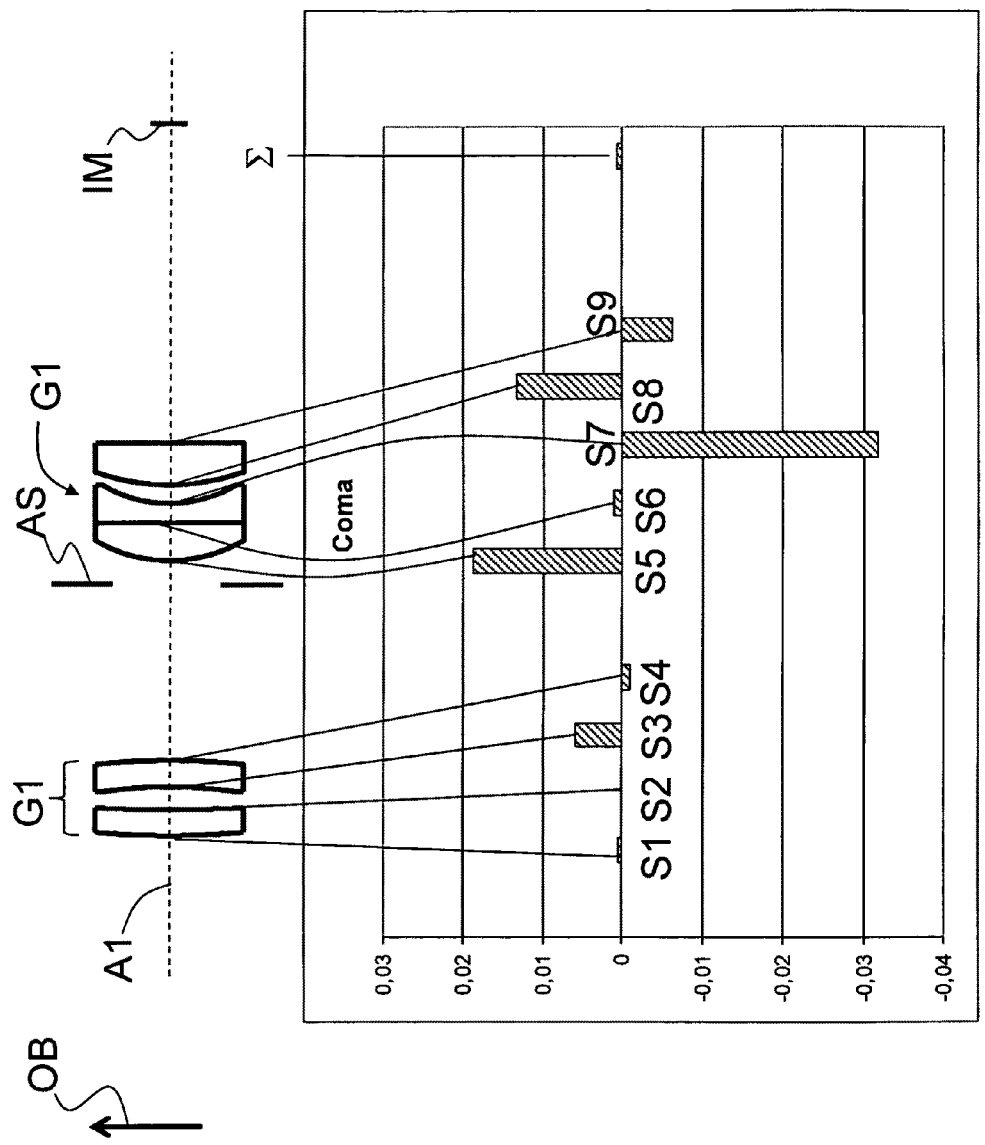
FIG. 4 is a schematic diagram of the amount of coma contributed by each surface of the example lens system, along with the total amount ("sum") as indicated by $\Sigma$.

Comatic aberration ("coma") can be the most disturbing and undesired aberration for imaging applications such as those contemplated by lens system 10. Coma reduces the MTF and sharpness of images across the field without providing any substantial gain in DOF. FIG. 4 is a schematic diagram of the contribution of coma (as represented by the second Seidel aberration) for each lens surface, along with the coma sum Σ, for the example lens system 10. Note that the sum Σ is far below 0.01λ and is closer to 0.001λ, which sums are considered negligible.

Select use of spherical aberration SA makes it possible to determine an axial position for aperture stop AS where the coma is null. As discussed above, in one example embodiment, lenses L1 and L2 of lens group G1 provide a small amount of spherical aberration SA sufficient to provide an aperture stop position $P_0$ where the residual coma is substantially reduced or even completely removed (to within a meaningful measurement).

Figure 5:
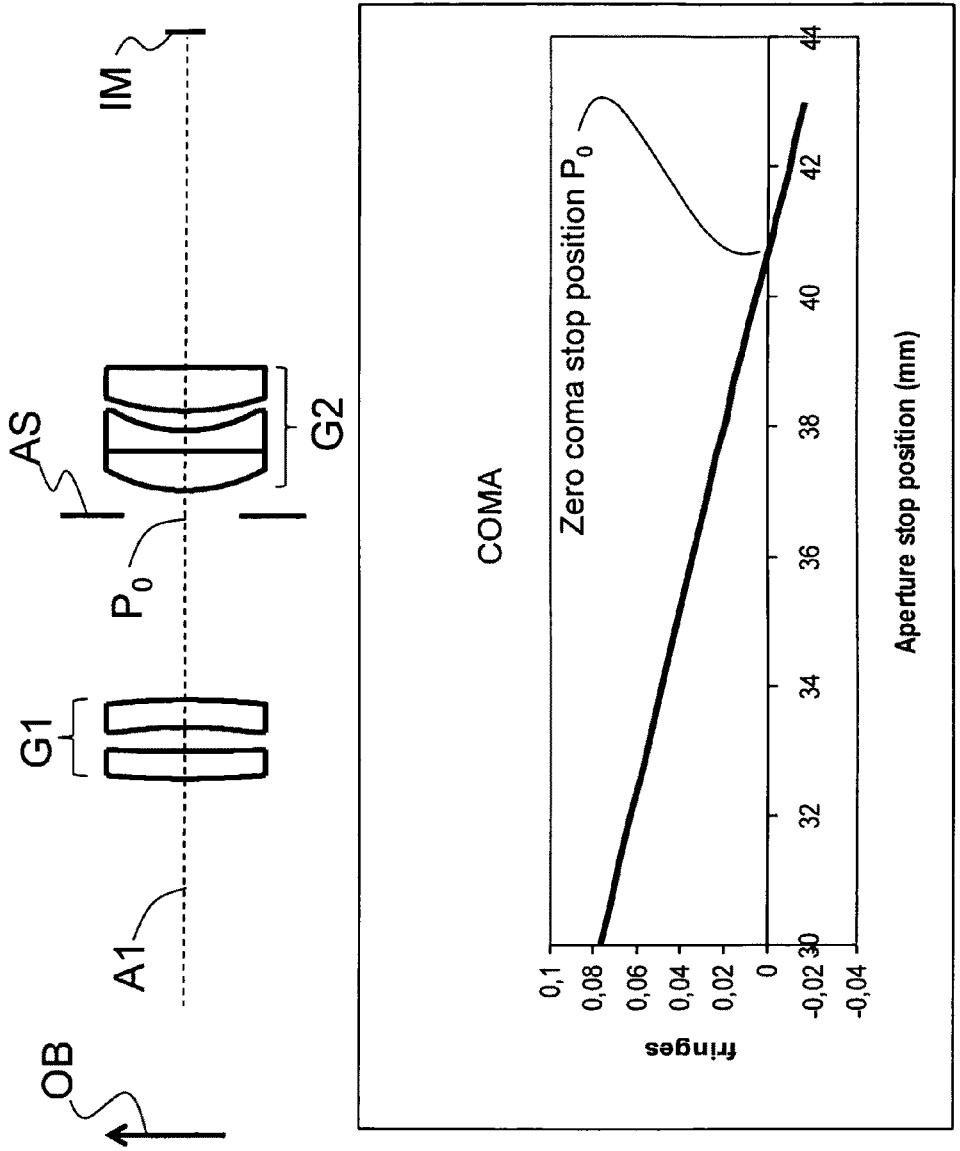
FIG. 5 is a schematic diagram of the evolution of coma with the aperture stop position that shows a zero coma position.

FIG. 5 is a schematic diagram of the evolution of coma with the aperture stop position and shows a zero coma position $P_0$. In an example embodiment, apertures stop AS is located at or near the zero coma position $P_0$, e.g., within a few millimeters. The configuration of lens system 10 thus allows for coma to be substantially reduced and effectively completely removed even if the total spherical aberration is null. However, it is desirable to produce a small amount of spherical aberration SA in the space between the groups G1 and G2 where stop aperture AS is located. The final amount (i.e., the sum Σ) of spherical aberration SA is set mainly by the surface curvatures of doublet D1.

Figure 6:
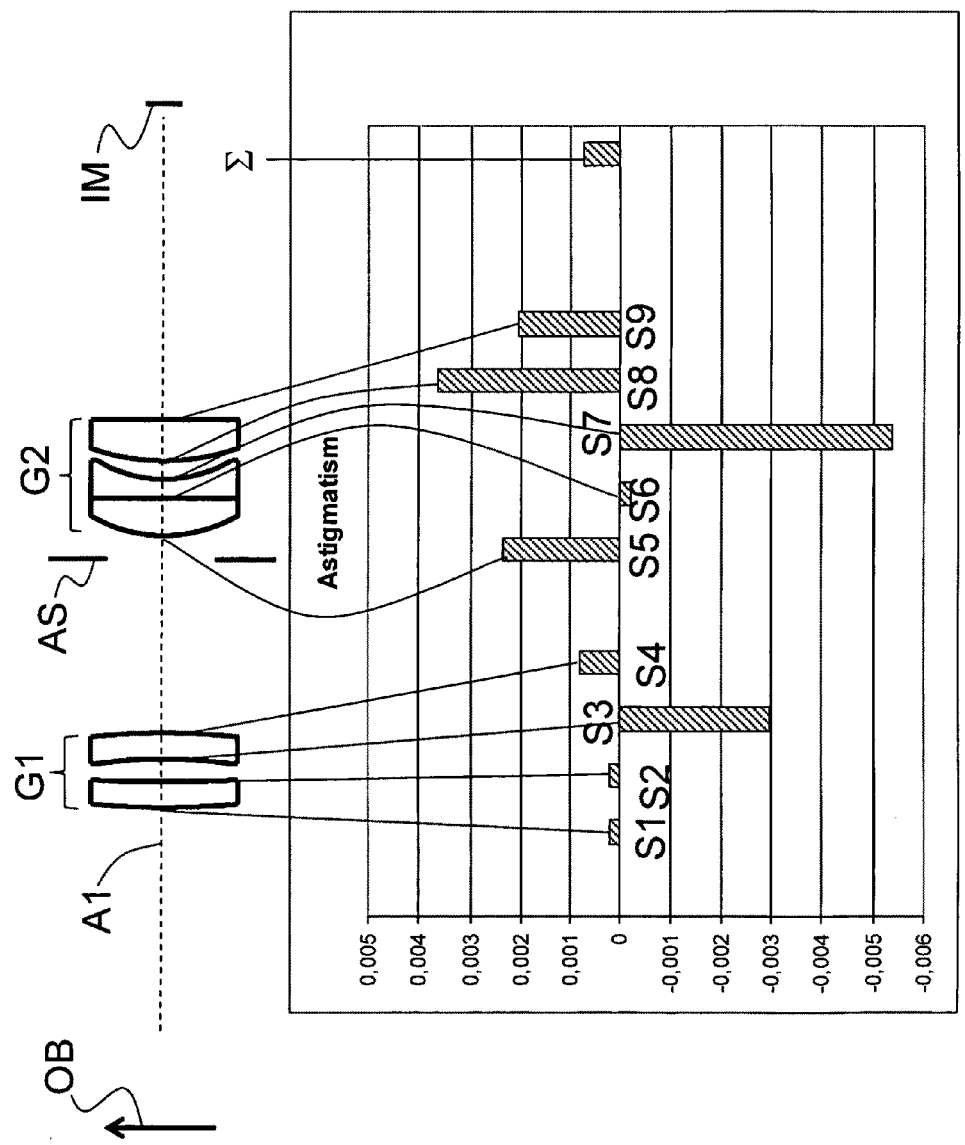
FIG. 6 is a schematic diagram of the amount of astigmatism contributed by each surface of the example lens system, along with the total amount ("sum") as indicated by $\Sigma$.

FIG. 6 is a schematic diagram of the contribution by each lens surface to astigmatic aberration or "astigmatism" (as represented by the third Seidel aberration) for the example lens system 10. Astigmatism is reduced by first group G1, specifically surface S3 of lens L2. The inverted meniscus lens makes a significant negative contribution to the astigmatism and compensates for the net positive contribution to astigmatism from second lens group G2.

Figure 7:
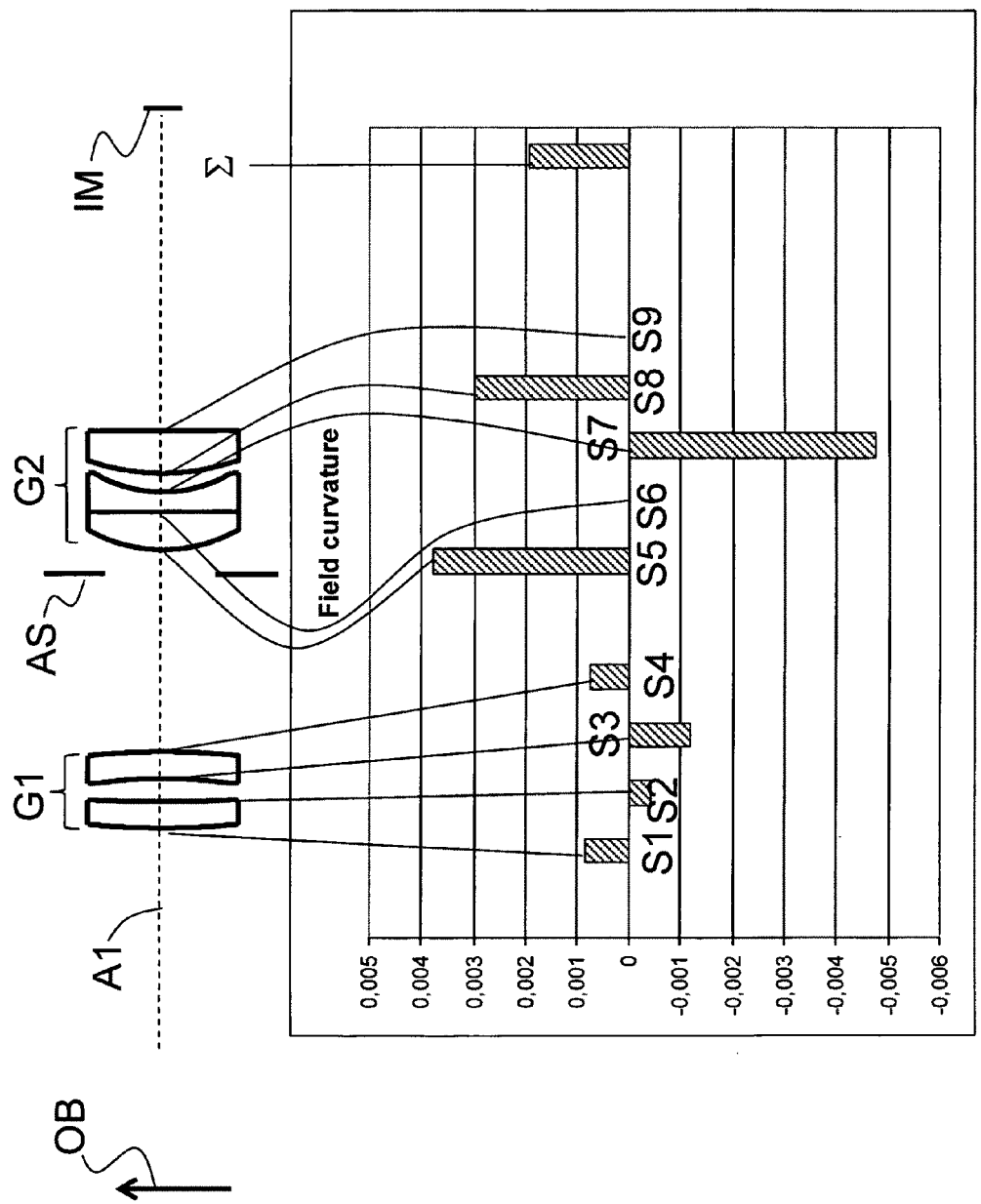
FIG. 7 is a schematic diagram of the amount of field curvature contributed by each surface of the example lens system, along with the total amount ("sum") as indicated by $\Sigma$.

FIG. 7 is a schematic diagram of the contribution by each lens surface to field curvature (as represented by the fourth Seidel aberration) for the example lens system 10. The field curvature is controlled by the Petzval sum. Surface S3 of lens L2 in first group G1 contributes a relatively large negative value to the Petzval sum. Negative lens L4 of doublet D1 produces the largest negative term to the Petzval sum, which reduces the overall field curvature sum. Thus, the choice of glass type for lens L4 is an important consideration.

It is noted here that there is a trade-off between the correction of field curvature and axial chromatic aberration. The correction of chromatic aberration requires a low Abbe number of less than 30 on the negative lens L4 of doublet D1 that is available with relatively high index glasses. On the other hand, correcting field curvature requires a relatively low index glass that precludes a very low Abbe number of less than 30. A reasonable compromise is to use glass type N-SF15 produced by SCHOTT ($N_d$=1.69892; $v_d$=30.2). Other glass types having close to these values are commercially available and can also be used as well.

The parameter range for lens system 10 for select lens characteristics is summarized in Table 1, below:

TABLE 1

PARAMETER RANGES

| PARAMETER | Min | Max |
| --- | --- | --- |
| Focal length FL | 20 mm | 800 mm |
| Aperture "F" number F/# | 1.4 | 16 |
| Spectral range | 400 nm | 2500 nm |
| Field diameter in image space | 4 mm | 25 mm |

Example Lens System

An example design for lens system 10 is set forth in Tables 2 and 3 and is suitable for surveillance applications (and is particularly well suited for CCTV cameras). The example lens has the following main parameter characteristics:

TABLE 2

PARAMETER RANGES

| Focal length | 86 mm |
| --- | --- |
| F# | 3.5 |
| Spectral range | 500 nm -1000 nm |
| Spherical aberration | 0.8 waves |
| Field diameter in image space | 8 mm |

TABLE 3

LENS DESIGN PARAMETERS

| # | Comment | Radius (mm) | Thickness (mm) | Glass | Diameter (mm) |
| --- | --- | --- | --- | --- | --- |
| 0 | Object | | infinite | | |
| 1 | L1 | 244.46 | 5.60 | N-LAF34 | 32.00 |
| 2 | | 724.24 | 5.00 | | 29.00 |
| 3 | L2 | −96.08 | 5.60 | N-PSK3 | 29.00 |
| 4 | | −156.04 | 40.00 | | 32.00 |
| 5 | Aperture stop | | 3.00 | | 24.49 |
| 6 | D1 | 32.04 | 8.00 | N-SK14 | 32.00 |
| 7 | | | 4.20 | N-SF15 | 32.00 |
| 8 | | 27.83 | 4.00 | | 29.00 |
| 9 | L3 | 48.03 | 9.00 | N-LAF36 | 32.00 |
| 10 | | | 69.29 | | 32.00 |
| 11 | image | | 0.00 | | 4.02 |

Figure 8:
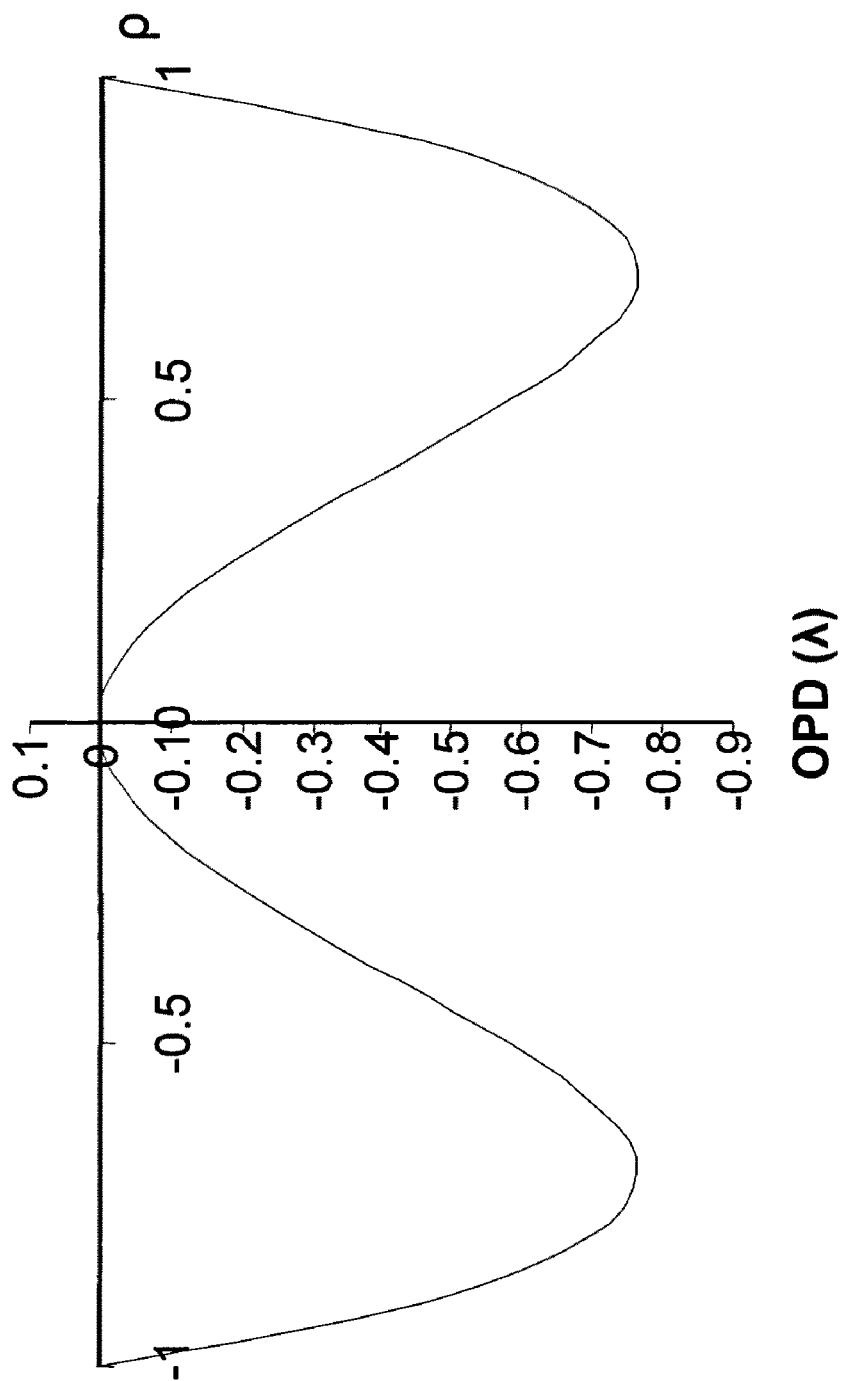
FIG. 8 is a schematic diagram of the optical path difference (OPD) across the pupil as a function of the normalized pupil coordinate $\rho$ for any point in the field of the lens system.

FIG. 8 is a schematic diagram of the optical path difference (OPD) in "waves" λ as a function of normalized pupil coordinate p across the pupil for any point in the field for lens system 10. The OPD shown in FIG. 8 has the signature of spherical aberration. An important characteristic of the design of lens system 10 is that spherical aberration SA be the main aberration over the field, and that is be substantially constant with field position. This characteristic maintains uniform image quality and EDOF over the entire image field. This characteristic is also evident in the listing in Table 4 of select Zernike coefficients, wherein Zernike coefficient $Z_9$ represents spherical aberration and is substantially larger than the other Zernike coefficients for astigmatism ($Z_5$ and $Z_6$) and for coma ($Z_7$ and $Z_8$).

TABLE 4

Zernike Coefficients

| | | Coefficient in waves ($\lambda$) | | |
|---|---|---|---|---|
| Zernike Coefficient | Aberration | Zernike polynomial term | Center of field | Half field (on X axis) | Edge of field for ⅓" image sensor (on X axis) |
| $Z_5$ | Astig X | $(p^2) * \cos(2A)$ | 0.000 | 0.000 | 0.000 |
| $Z_6$ | Astig Y | $(p^2) * \sin(2A)$ | 0.000 | −0.070 | −0.238 |
| $Z_7$ | coma X | $(3p^2 - 2) p * \cos(A)$ | 0.000 | 0.005 | 0.007 |
| $Z_8$ | coma Y | $(3p^2 - 2) p * \sin(A)$ | 0.000 | 0.000 | 0.000 |
| $Z_9$ | Spherical Aberration | $(6p^4 - 6p^2 + 1)$ | 0.511 | 0.504 | 0.487 |

Lens system 10 also has a number of advantages, such as a low manufacturing cost (e.g., by using off-the-shelf lens elements), a relatively large field due to reduced field aberrations. Imaging system 8 also presents the option of performing digital image processing using linear filtering in the frequency domain.

The exact amount of spherical SA in lens system 10 may vary according to the amount of axial chromatic aberration present, depending of the Abbe number of the optical material of the negative lens in the second lens group, and the spectral bandwidth used for imaging.

Image Processing

With reference again to FIG. 1, EDOF imaging system 8 includes the aforementioned image sensor 30, which has a photosensitive surface 32 (e.g., an array of charge-coupled devices) arranged at image plane IP so that the image sensor receives and detects image IM. In this situation, image IM is also referred to herein as an "initial" or a "raw" image. In an example embodiment, image sensor 30 is or otherwise includes a high-definition CCD camera or CMOS camera. In an example embodiment, photosensitive surface 32 is made up of 3000×2208 pixels, with a pixel size of 3.5 microns. The full-well capacity is reduced to 21,000 electrons for a CMOS camera at this small pixel size, which translates into a minimum of shot noise of 43.2 dB at saturation level. An example image sensor 30 is or includes a camera from Pixelink PL-A781 having 3000×2208 pixels linked by IEEE1394 Fire Wire to an image processor (discussed below), and the application calls API provided by a Pixelink library in a DLL to control the camera perform image acquisition.

In an example embodiment, EDOF imaging system 8 further includes a controller 50, such as a computer or like machine, that is adapted (e.g., via instructions such as software embodied in a computer-readable or machine-readable medium) to control the operation of the various components of the system. Controller 50 is configured to control the operation of EDOF imaging system 10 and includes an image processing unit ("image processor") 54 electrically connected to image sensor 30. Image processor 54 is adapted to receive and process digitized raw image signals SRI from image sensor 30 and form therefrom processed image signals SPI, as described in greater detail below.

In an example embodiment, controller 50 is or includes a computer with a processor (e.g., image processor 54) and includes an operating system such as Microsoft WINDOWS or LINUX.

In an example embodiment, image processor 54 is or includes any processor or device capable of executing a series of software instructions and includes, without limitation, a general- or special-purpose microprocessor, finite state machine, controller, computer, central-processing unit (CPU), field-programmable gate array (FPGA), or digital signal processor. In an example embodiment, the processor is an Intel XEON or PENTIUM processor, or an AMD TURION or other processor in the line of such processors made by AMD Corp., Intel Corp. or other semiconductor processor manufacturer.

Controller 50 also preferably includes a memory unit ("memory") 56 operably coupled to image processor 54. As used herein, the term "memory" refers to any processor-readable medium or computer-readable medium, including but not limited to RAM, ROM, EPROM, PROM, EEPROM, disk, floppy disk, hard disk, CD-ROM, DVD, or the like, on which may be stored a series of instructions executable by image processor 54. In an example embodiment, controller 50 includes a port or drive 60 adapted to accommodate a removable processor-readable medium 61, such as CD-ROM, DVE, memory stick or like storage medium.

The EDOF methods implemented in EDOF imaging system 8 of the present invention may be implemented in various embodiments in a machine-readable medium (e.g., memory 56) comprising machine readable instructions (e.g., computer programs and/or software modules) for causing controller 50 to perform the methods and the controlling operations for operating system 10. In an example embodiment, the computer programs run on image processor 54 out of memory 56, and may be transferred to main memory from permanent storage via disk drive or port 60 when stored on removable media 61, or via a network connection or modem connection when stored outside of controller 50, or via other types of computer or machine-readable media from which it can be read and utilized.

The computer programs and/or software modules may comprise multiple modules or objects to perform the various methods of the present invention, and control the operation and function of the various components in EDOF imaging system 8. The type of computer programming languages used for the code may vary between procedural code-type languages to object-oriented languages. The files or objects need not have a one to one correspondence to the modules or method steps described herein, depending on the desires of the programmer. Further, the method and apparatus may comprise combinations of software, hardware and firmware. Firmware can be downloaded into image processor 54 for implementing the various example embodiments of the invention.

Controller 50 also optionally includes a display 66 that can be used to display information using a wide variety of alphanumeric and graphical representations. For example, display 66 is useful for displaying extended images. Controller 50 also optionally includes a data-entry device 68, such as a keyboard, that allows a user of system 10 to input information into controller 50 (e.g., the name of the object being imaged, and to manually control the operation of system 10. It is noted here that controller 50 may be sized to be portable, e.g., as a hand-held device, or built in to a camera housing (not shown).

System 10 also optionally includes a database unit 90 operably connected to controller 50. Database unit 90 includes a memory unit 92 that serves as a computer-readable medium adapted to receive processed image signals SPI from image processor 54 and store the associated processed digital images of object OB as represented by the processed image signals. Memory unit ("memory") 92 may be any computer-readable medium, including but not limited to RAM, ROM, EPROM, PROM, EEPROM, disk, floppy disk, hard disk, CD-ROM, DVD, or the like, on which data may be stored. In an example embodiment, database unit 90 is included within controller 50. In an example embodiment, memory unit 92 is the same as memory unit 56, i.e., memory unit 56 serves to store processed digital images based on processed image signals SPI.

General Method of Operation

With reference to FIG. 1, in the general operation of EDOF imaging system 8, image IM of object OB is formed on photosensitive surface 32 of sensor 30 by lens system 10. Controller 50 sends a control signal S30 to activate image sensor 30 for a given exposure time so that image IM is captured by photosensitive surface 32. Image sensor 30 digitizes this "raw" image IM and creates the electronic raw image signal SRI representative of the raw captured image. In an example embodiment, raw image IM is a video image and raw image signal SRI is a video stream that includes one or more video frames.

At this point, in one example embodiment, raw image IM is used directly, i.e., without any image processing, or with only minor image processing that does not involve MTF-based image enhancement, as discussed below. This approach can be used for certain types of imaging applications, such as character recognition and for imaging binary objects (e.g., bar-code objects) where, for example, determining edge location is more important than image contrast. The raw image IM embodied in raw image signal SRI is associated with an EDOF provided by ΣDOF lens system 10 even without additional contrast-enhancing image processing, so that in some example embodiments, EDOF imaging system 8 need not utilize the image-processing portion of the system. In an example embodiment, a number N of raw images IM are collected via raw image signals SRI and are averaged (e.g., using image processor 54) in order to form a (digitized) raw image IM' (and corresponding raw image signal SRI') that has reduced noise as compared to any one of the N raw images.

In other example embodiments where the raw image IM is not directly usable, image processor 54 receives and digitally processes the electronic raw image signal SRI to form a corresponding contrast-enhanced image embodied in an electronic processed-enhanced image signal SPI, which is used directly (e.g., displayed on display 66, which may be at a remote location from controller 50, etc.) or optionally stored in database unit 90. In another example embodiment, controller 50 is at a remote location relative to lens system 10.

In one aspect of the invention, the image processing is not necessarily applied to all frames on a video stream, or to all images. For example, the imaging-system user can select some interesting frames stored on the computer-readable medium and process them. This allows for the system user to create high-resolution enhanced images and observe small details in the image that require an enhanced MTF. The image processing does not require the use of a specialized high-speed digital signal processor because delivery of an enhanced image in a matter of a few second is not generally a problem for the imaging system user. The image processing can also be made faster by selecting a region of interest in the image that doesn't cover the entire image. For example, if an imaging-system user is reviewing a picture of a car and only wishes to see the license plate number, only the license plate portion of the image can be processed and the enhanced close-up image portion analyzed. In an example embodiment, this processed image is displayed on display 66 and is optionally stored in memory unit 56.

Image processor 54 is adapted to receive from image sensor 30 digitized electrical raw image signals SRI and process the corresponding raw images to form processed, contrast-enhanced images. This is accomplished by filtering the raw images in a manner that restores the MTF as a smooth function that decreases continuously with spatial frequency and that preferably avoids overshoots, ringing and other image artifacts.

Noise amplification is often a problem in any filtering process that seeks to sharpen a signal (e.g., enhance contrast in a digital optical image). Accordingly, in an example embodiment, an optimized gain function (similar to Wiener's filter) that takes in account the power spectrum of noise is applied to reduce noise amplification during the contrast-enhancement process.

In an example embodiment, the gain function applied to the "raw" MTF to form the "output" or "extended" MTF (denoted herein as MTF') depends on the object distance $D_{OB}$. The MTF versus distance $D_{OB}$ is acquired by a calibration process wherein the MTF is measured in the expected depth of field DOF by sampling using defocus steps $\delta_F \leq (1/8)(\lambda/(NA^2))$ to avoid any undersampling and thus the loss of through-focus information for the MTF. In this instance, output MTF' is said to be "focus-dependent."

Figure 9:
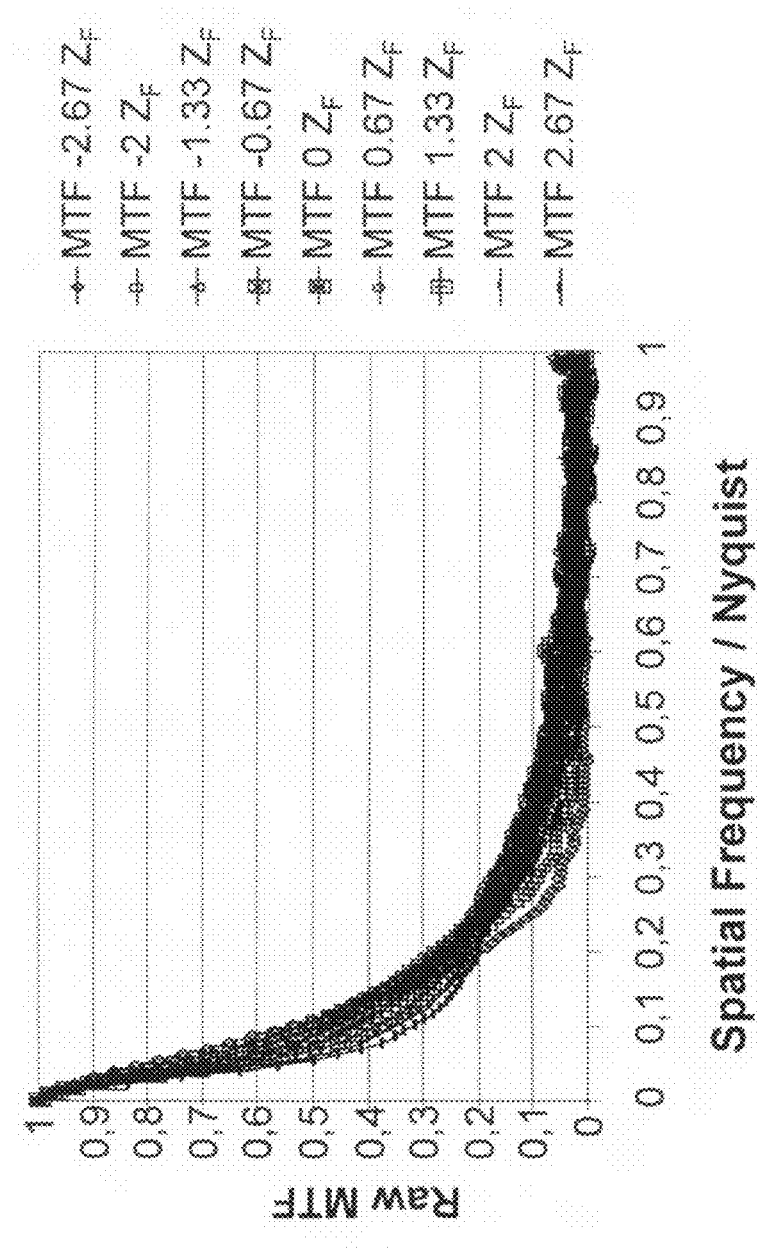
FIG. 9 is the plot of the raw optical MTF at various distances from the best focus, wherein the defocus distance step is $\delta_F = 1.33 \cdot Z_F$, where $Z_F$ is the Fresnel distance defined as $$Z_F = \frac{\lambda}{NA^2};$$

Basically, the MTF is restored accordingly to the defocusing distance when known by measurement or from any information that can be extracted from the image. FIG. 9 is the plot of the raw optical MTF at various distances from the best focus, wherein the defocus distance step $\delta_F$ is $1.33 \cdot Z_F$, where $Z_F$ is the Fresnel distance defined as $$Z_F = \frac{\lambda}{NA^2},$$

where NA the numerical aperture in the space where the defocus is measured (i.e., "image space"). The raw MTF plots for different focus distances illustrate the MTF dispersion that occurs due to defocus. For each step through defocus, a digital filtering function is used to restore the best MTF for the processed image according to the measured MTF. The use of this filter requires knowing the amount of defocus, which can be measured using any one of a number of available techniques known in the art. The filter used between defocus steps $\delta_F$ is the linear interpolation of the adjacent focus steps.

MTF Restoration

The above-mentioned MTF gain function used to restore or enhance the raw MTF is a three-dimensional function G(u, v, d), wherein u is the spatial frequency along the X axis, v is the spatial frequency along the Y axis, and d is the distance of the object in the allowed extended depth of field DOF (d thus corresponds to the object distance $D_{OB}$). The rotational symmetry of the PSF and MTF results in a simplified definition of the gain function, namely:

$$G'(\omega,d) \text{ with } \omega^2=u^2+v^2$$

The rotational symmetry also makes G'(w, d) a real function instead of a complex function in the general case.

The "extended" or "restored" OTF is denoted OTF' and is defined as:

$$OTF'(u,v,d)=G(u,v,d)OTF(u,v,d)$$

where OTF is the Optical Transfer Function lens system 10 for incoherent light. The OTF' is the equivalent OTF of the imaging system including the digital processing, and G is the aforementioned MTF gain function. The relationship for the output MTF' based on the original or unrestored MTF is given by:

$$MTF'(\omega,d)=G'(\omega,d)MTF(\omega,d)$$

Figure 10B:
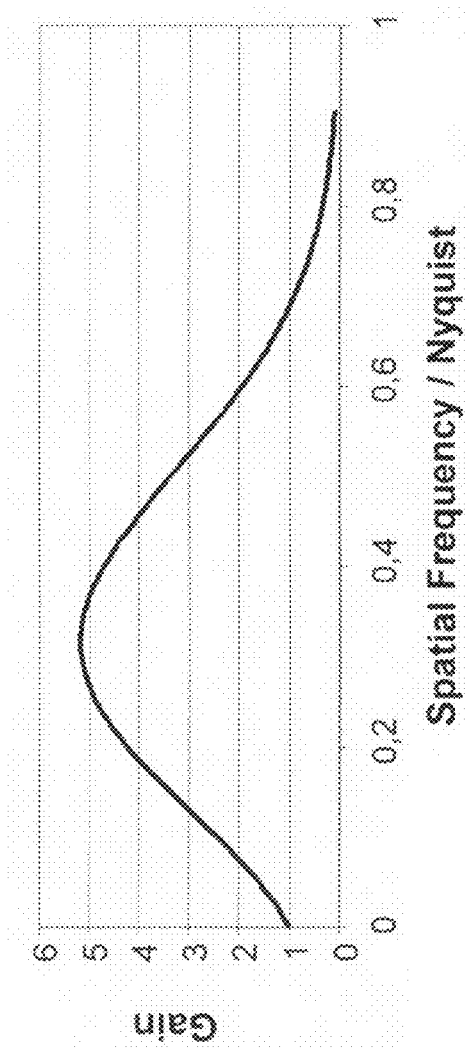
FIG. 10B is the plot of the average (i.e., constant with focus) gain function of the spatial frequency that is applied on the raw MTF when the defocus distance is unknown.
Figure 11B:
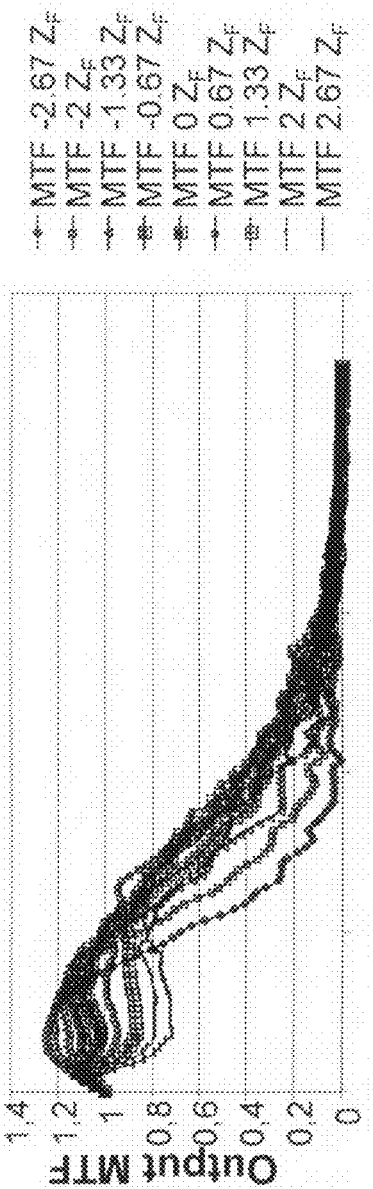
FIG. 11B is the plot of the enhanced MTF produced by the multiplication of the raw MTF of FIG. 9 by the average gain function of FIG. 10B.

When the object distance is unknown, an optimized average gain function G' can be used, as shown in FIG. 10B. In this case, G' is constant through focus and the output MTF' is extended, but is not a function of the object distance. The resultant output MTF' improves image contrast, albeit with degraded performance as compared to the focus-dependent gain function case. This simplified output MTF' is effective for simplified image processing where the distance information is not extracted from the image. The shape of the resultant output MTF' is shown in FIG. 11B and is variable with focus distance, and some overshoots and ringing occurs. These artifacts, while undesirable, are acceptable for most basic CCTV applications.

The after-digital process is preferably optimized to deliver substantially the same output MTF' at any distance in the range of the working depth of field DOF. This provides a substantially constant image quality, independent of object distance $D_{OB}$, so long as $D_{OB}$ is within the depth of field DOF of lens system 10. Because lens system 10 has an EDOF due to the presence of spherical aberration as described below, lens system 10 can accommodate a relatively large variation in object distance $D_{OB}$ and still be able to capture suitable images.

FIG. 10A plots through focus the typical focus-dependent gain in output MTF' obtained using the above-described process. FIG. 11A plots the typical output MTF' for the different focus positions. The shape of the output MTF' is close as possible of the hypergaussian function, namely:

$$MTF'(\omega, d) = \exp\left(-\left(\frac{\omega}{\omega_c}\right)^{2n}\right)$$

wherein n is the hypergaussian order, $w_c$ is the cutoff frequency, which is set at the highest frequency where the raw MTF is higher that 5% on the whole range of the extended depth of field DOF.

If n=1, the output MTF' is Gaussian. This provides a PSF, LSF (line-spread function) and ESF (edge-spread function) without any ringing or overshoot. If n>1, the output MTF' is a hypergaussian. For higher values of n, the contrast in high spatial frequencies is also high, but the occurrence of ringing and overshoot increases. A good compromise is n=2, wherein the output MTF' is well extended at low and medium spatial frequencies, while the ringing and overshoot are limited to about 3%, which is acceptable for most imaging applications.

The real output MTF' is as close as possible to a hypergaussian, and is determined by an optimization process that involves a merit function M, which is defined as:

$$M = A_0 \cdot \int_0^{Fc}\left(MTF'(\omega, d) - \exp\left(-\left(\frac{\omega}{\omega_c}\right)^{2n}\right)^2\right)d\omega + A_1 \cdot \int G'(\omega, d)^2 d\omega + A_2 \cdot \Delta os^2$$

Merit function M is minimized by using, for example, a Newton optimization algorithm. The first term with the coefficient $A_0$ minimizes the deviation from the hypergaussain output MTF'. The second term with the coefficient $A_1$ controls the power noise amplification. The third term with the coefficient $A_2$ controls the overshoot amplification.

Figure 12:
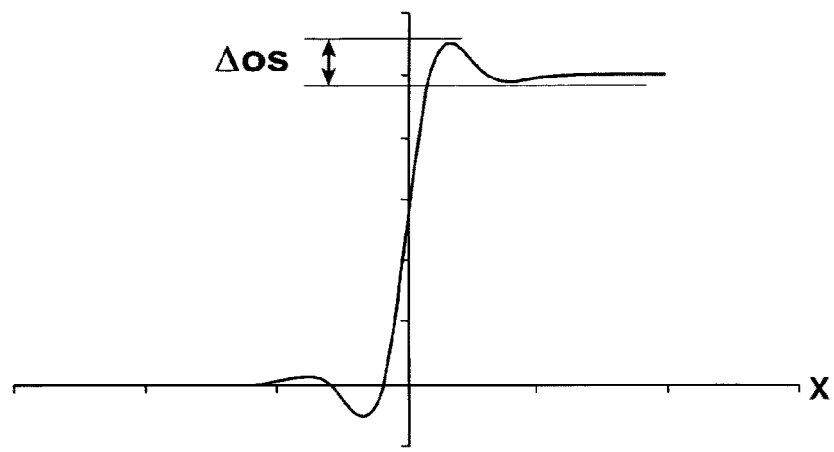
FIG. 12 is a plot of the intensity I versus position for the image of an edge, showing the overshoot $\Delta os$ caused by ringing in the image.

It is important to control the power noise amplification. At distances where the gain on the raw MTF is higher in order to achieve the output MTF', a good compromise between the MTF level and the signal-to-noise ratio on the image can be determined, while controlling the slope of the output MTF' at high special frequencies avoids significant overshoot. The third term in the merit function M is the square of the relative overshoot on an edge spread, which is illustrated in FIG. 12, wherein the overshoot is given by $\Delta$os.

Figure 13:
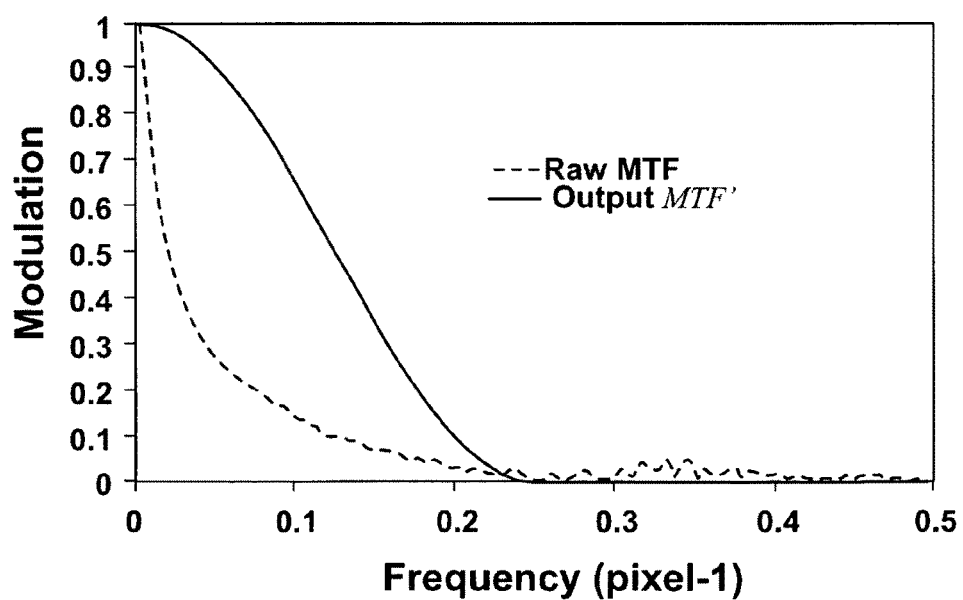
FIG. 13 plots the raw MTF and output MTF' at best focus to illustrate the recovery of image resolution (contrast) via image processing.

FIG. 13 is a plot of the raw MTF (dashed line) along with an output MTF' (solid line) formed using the process described above. The output MTF' has a smooth shape that avoids overshoots and other imaging artifacts. The applied gain of the digital filter is optimized or extended to obtain the maximum output MTF' while controlling the gain or noise.

In an example embodiment, the raw MTF is measured for calibration at different sampled distances that overlap the EDOF by using a slanted edge with a uniform incoherent backlighting at the same spectrum used during image capture.

As discussed above, the gain function applied in the spatial frequency domain FIG. 10A produces output MTF, shown in FIG. 10B. The output MTF' of FIG. 10B has a continuous, relatively shallow slope that provides good image contrast image with minimal or no overshoot, ringing or other artifacts. This produces an almost constant output MTF' through the EDOF. The scale of defocus is normalized by the Fresnel distance $Z_F$ to get a general rule of the invention applied to any aperture. Also, the scale of spatial frequency (x-axis) is normalized by the Nyquist frequency of the image sensor, as 1/(2×P), where P is the pixel pitch. Good results are obtained when the pixel size and the matching Nyquist frequency are close to the optical cut-off frequency, which depends on the imaging wavelength $\lambda$ and the numerical aperture NA in the image space. It is desirable to get an optical MTF close to zero at the Nyquist frequency to avoid aliasing. On the other hand, having a higher Nyquist frequency produces an oversampled image, as the resolution is limited by the optical MTF only. This means a higher numerical aperture NA in the image space is required for image sensors with a small pixel size.

Image Noise Reduction by Averaging Sequential Images

There are two distinct sources of noise associated with the image acquisition and image processing steps. The first source of noise is called "fixed-pattern noise" or FP noise for short. The FP noise is reduced by a specific calibration of image sensor 30 at the given operating conditions. In an example embodiment, FP noise is reduced via a multi-level mapping of the fixed pattern noise wherein each pixel is corrected by a calibration table, e.g., a lookup table that has the correction values. This requires an individual calibration of each image sensor and calibration data storage in a calibration file. The mapping of the fixed pattern noise for a given image sensor is performed, for example, by imaging a pure white image (e.g., from an integrating sphere) and measuring the variation in the acquired raw digital image.

The other source of noise is shot noise, which is random noise. The shot noise is produced in electronic devices by the Poisson statistics associated with the movement of electrons. Shot noise also arises when converting photons to electrons via the photo-electric effect.

Some imaging applications, such as high-resolution security imaging, require a high-definition image sensor 30. To this end, in an example embodiment, image sensor 30 is or includes a CMOS or CCD camera having a large number of pixels, e.g., an array of 3000×2208 pixels with a pixel size of 3.5 µm. The full well capacity in such an image sensor is reduced to 21,000 electrons for a CMOS camera at this small pixel size, and the associated minimum of shot noise is about 43.2 dB at the saturation level.

An example embodiment of EDOF imaging system 8 has reduced noise so that the MTF quality is improved, which leads to improved processed images. The random nature of the shot noise is such that averaging N captured images is the only available approach to reducing the noise (i.e., improving the SNR). The noise decreases (i.e., the SNR increases) in proportion to $N^{1/2}$. As discussed above, this averaging process can be applied to raw images, as well as to processed (i.e., contrast-enhanced) images.

Averaging N captured images is a suitable noise reduction approach so long as the images being averaged are of a fixed object or scene, which is often the case for surveillance applications. However, such averaging is problematic when the object moves. In an example embodiment, the movement of object OB is tracked and accurately measured, and the averaging process for reducing noise is employed by accounting for and compensating for the objection motion prior to averaging the raw images.

In an example embodiment, the image-averaging process of the present invention uses a correlation function between the sequential images at a common region of interest. The relative two-dimensional image shifts are determined by the location of the correlation peak. The correlation function is processed in the Fourier domain to speed the calculation by using a fast-Fourier transform (FFT) algorithm. The correlation function provided is sampled at the same sampling intervals as the initial images. The detection of the correlation maximum is accurate to the size of one pixel.

An improvement of this measurement technique is to use a 3×3 kernel of pixels centered on the pixel associated with the maximum correlation peak. The sub-pixel location is determined by fitting to two-dimensional parabolic functions to establish a maximum. The (X,Y) image shift is then determined. The images are re-sampled at their shifted locations. If the decimal part of the measured (X,Y) shift is not equal to 0, a bi-linear interpolation is performed. It is also possible to use a Shannon interpolation as well because there is no signal in the image at frequencies higher than the Nyquist frequency. All the images are then summed after being re-sampled, taking in account the (X,Y) shift in the measured correlation.

The MTF can also be used in conjunction with the PSF to characterize the EDOF' by examining the resolution R and image contrast CI of the image through focus. Here, the image contrast is given by:

$$CI = (I_{MAX} - I_{MIN})/(I_{MAX} + I_{MIN})$$

and is measured for an image of a set of sinusoidal line-space pairs having a particular spatial frequency, where $I_{MAX}$ and $I_{MIN}$ are the maximum and minimum image intensities, respectively. The "best focus" is defined as the image position where the MTF is maximized and where the PSF is the narrowest. When a lens system is free from aberrations (i.e., is diffraction limited), the best focus based on the MTF coincides with the best focus based on the PSF. However, when aberrations are present in a lens system, the best focus positions based on the MTF and PSF can differ.

Conventional lens design principles call for designing a lens system in a manner that seeks to eliminate all aberrations, or to at least balance them to minimize their effect so that the lens system on the whole is substantially free of aberrations.

Figure 14A:
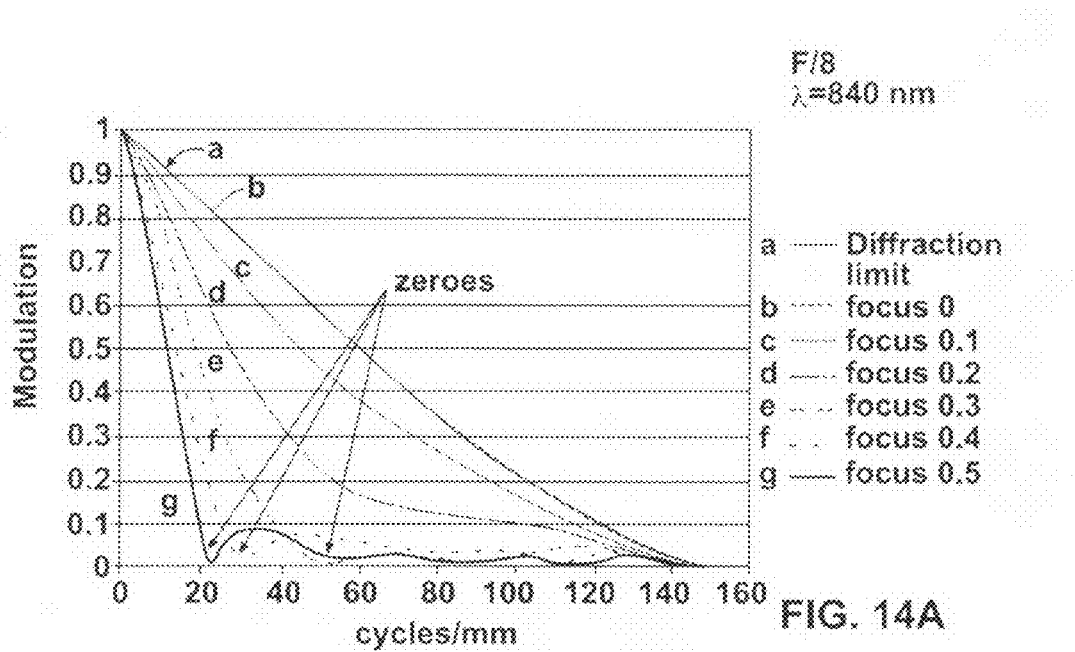
FIG. 14A is a plot of the diffraction-limited MTF for an ideal imaging system for varying amounts of defocus as indicated by curves a through g.
Figure 14B:
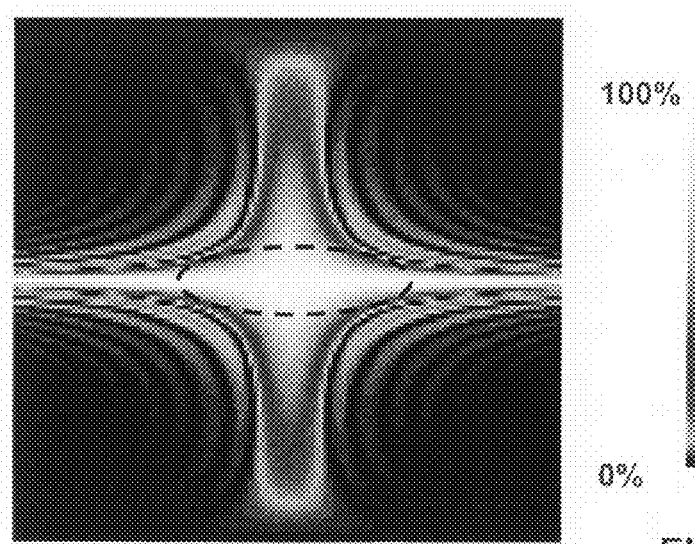
FIG. 14B is a gray-scale plot of the MTF distribution through focus (horizontal axis) for an idealized imaging optical system, with the dashed ellipse indicating an approximate depth of focus and the vertical axis indicating spatial frequency.
Figure 15A:
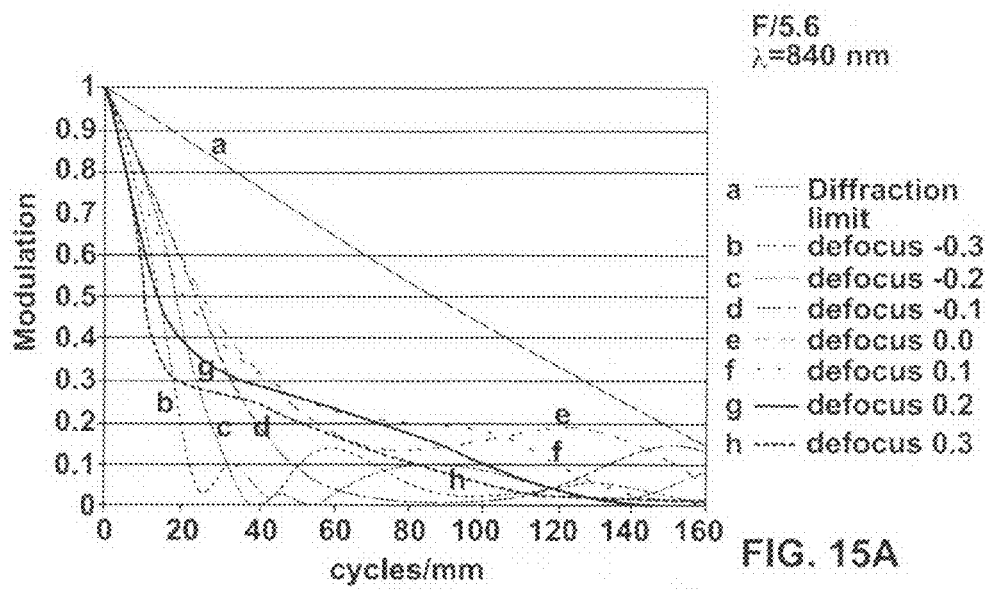
FIG. 15A is a plot of the MTF for varying amounts of defocus for an imaging optical system having an amount of spherical aberration SA=0.75λ, along with the zero-focus diffraction limited MTF for comparison, as indicated by curves a through h.
Figure 15B:
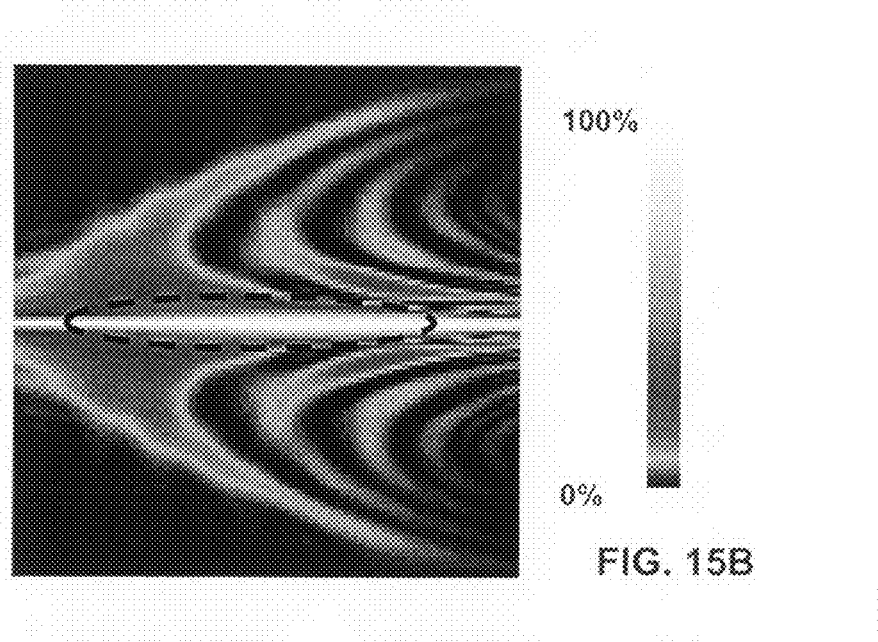
FIG. 15B is the same type of gray-scale through-focus MTF plot as FIG. 14B, but for the MTF of FIG. 15A, illustrating how the depth of focus (dashed line) is axially extended as compared to the diffraction-limited case of FIG. 14B by virtue of the presence of spherical aberration.

However, in the present invention, lens system 10 is intentionally designed to have spherical aberration as a dominant aberration in the amounts set forth above, and optionally can have a small amount of chromatic aberration as well. FIG. 14A is a plot of the MTF for an F/8 lens without aberrations (curves a through g), while FIG. 15A is a plot of an MTF for an F/5.6 lens that has SA=0.75λ (curves a through h). FIG. 14B is a gray-scale plot of the MTF through focus for the diffraction-limited case of the F/8 lens of FIG. 8A, and FIG. 15B is a similar gray-scale plot of the MTF through focus for the F/5.6 lens with the spherical aberration SA of FIG. 15A.

The spherical aberration reduces the contrast of the image by reducing the overall level of the MTF from the base frequency $f_0=0$ to the cutoff frequency $f_C$. The cut off frequency $f_C$ is not significantly reduced as compared to the ideal (i.e., diffraction-limited) MTF, so nearly all the original spatial-frequency spectrum is available. Thus, the spatial-frequency information is still available in the image, albeit with a lower contrast. The reduced contrast is then restored by the digital filtering process as carried out by image processing unit 54, as described above.

The amount of spherical aberration SA results in an EDOF in the sense that the high spatial frequencies stay available over a greater range of defocus. The digital filtering restores the contrast over the EDOF, thereby effectively enhancing the imaging performance of lens system 10 as compared to its diffraction-limited counterpart.

Spherical aberration is an "even" aberration in the sense that the wavefront "error" is given by $W(\rho)=\rho^4$, wherein ρ is the normalized pupil coordinate. Thus, spherical aberration presents a rotationally symmetric wavefront so that the phase is zero. This means that the resulting OTF (which is the Fourier Transform of the PSF) is a rotationally symmetric, real function. The MTF, which is the magnitude of the OTF, can be obtained where spherical aberration is the dominant aberration by considering a one-dimensional MTF measurement taken on a slanted edge. This measurement provides all the required information to restore the two-dimensional image via digital signal processing. Also, the phase is zero at any defocus position, which allows for digital image processing to enhance the MTF without the need to consider the phase component (i.e., the phase transfer function, or PFT) of the OTF in the Fourier (i.e., spatial-frequency) space.

As can be seen from FIG. 15A, because the image-wise side of the defocus (as measured from the "best focus" plane) has no zero in the MTF when there is spherical aberration present, there is no contrast inversion. This allows for an image to be formed and detected in the EDOF' (see dashed ellipse in FIG. 15B) and to be restored without having to account for detrimental ringing, overshoot or other image artifacts.

An amount of spherical aberration SA of about 0.75λ gives a significant DOF enhancement without forming a zero in the MTF on one defocus side. Beyond about SA=0.75λ, a zero occurs on both sides of defocus from the best focus position. For a diffraction-limited optical system, the depth of focus DOF' is given by the relationship DOF'=±λ/(NA$^2$), where NA is the numerical aperture of the optical system. In an example embodiment, lens system 10 has an NA between about 0.033 and 0.125 (i.e., about F/15 to about F/4, where F/#=1/(2NA) assuming the small-angle approximation).

By way of example, for F/6.6, a center imaging wavelength of λ=800 nm and a bandwidth of Δλ, the diffraction-limited depth of focus DOF' is about 20 mm, with a transverse magnification of 1/1.4. The introduction of spherical aberration SA=0.75λ increases the depth of focus DOF' to about 100 mm, an increase of about 5×.

Figure 15C:
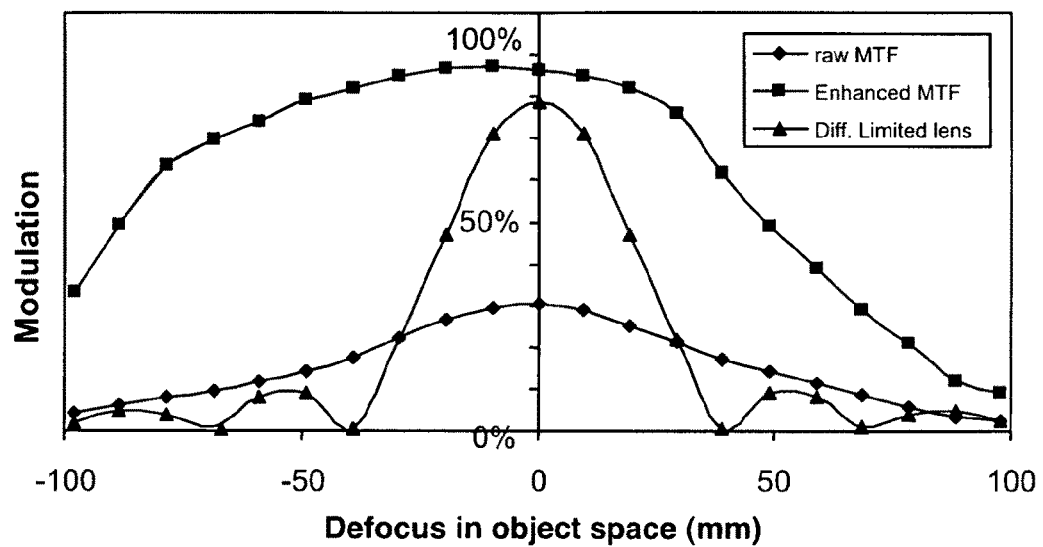
FIG. 15C plots the through-focus MTF at 3 line-pairs per millimeter (lp/mm) in object space for NA=0.0063 for the raw MTF, the MTF' and the diffraction-limited MTF.
Figure 16A:
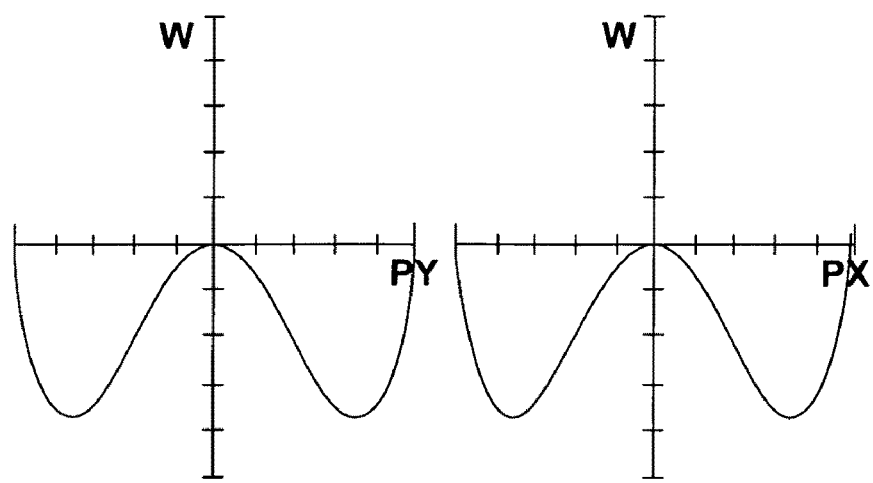
FIGS. 16A-16D are plots of the OPD for various image heights (0 mm, 20 mm, 30 mm and 60 mm, respectively) for a lens system with SA=0.7λ.
Figure 16B:
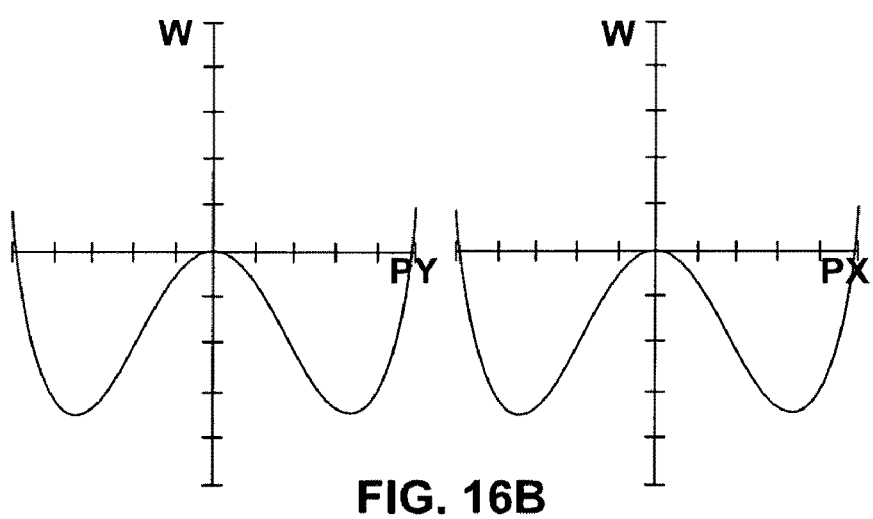
Figure 16C:
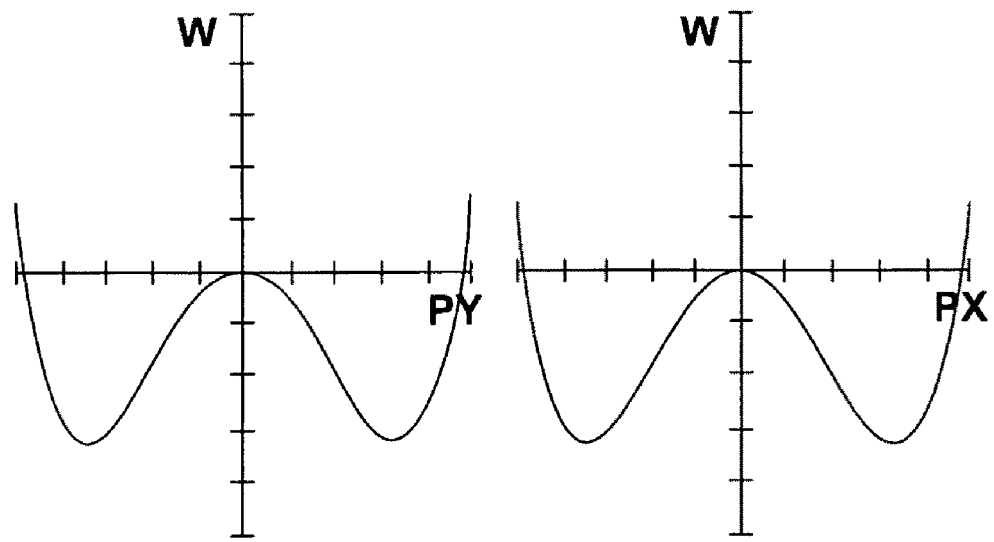
Figure 16D:
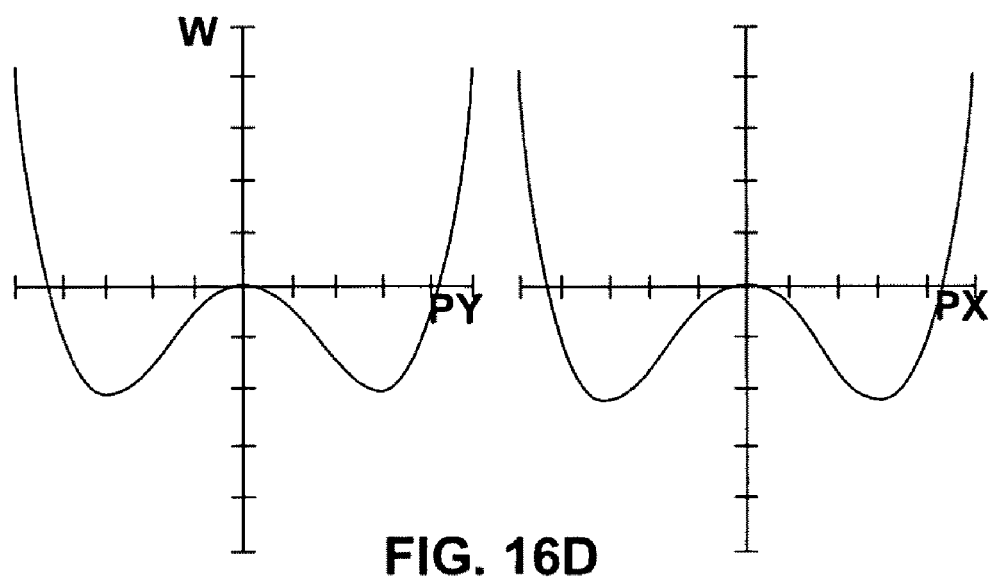

FIG. 15C plots the through-focus MTF at 3 lp/mm in object space for NA=0.0063 for the raw MTF, the output MTF' and the diffraction-limited MTF.

FIGS. 16A-16D are plots of the optical path difference (OPD) for various image heights (0 mm, 20 mm, 30 mm and 60 mm, respectively) for an example lens system 10 having an amount of spherical aberration SA=0.7λ. The OPD plots show the characteristics of spherical aberration, which is substantially constant as a function of field position (image heights).

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. An imaging system for imaging an object within an extended depth-of-field (EDOF) at an imaging wavelength λ, comprising along an optical axis:
   a lens system having a total lens power $\phi_T$ and an amount of spherical aberration SA, wherein 0.5λ≦SA≦1λ, the lens system comprising:
   a) a first most objectwise lens group that consists of first and second confronting meniscus lens elements that have an overall optical power $\phi_1$ such that $|\phi_1/\phi_T|$≦0.05;
   b) a second most imagewise lens group comprising three lens elements, where two of the lens elements form a doublet that includes one negative lens element;
   c) an aperture stop arranged either between the first and second lens groups or within the second lens group; and
   an image sensor arranged to receive the image and form therefrom a digitized electronic raw image; and
   a controller arranged to send a control signal to activate said image sensor so that an image may be captured by a photosensitive surface of said image sensor.

2. The imaging system of claim 1, further comprising;
   an image processor electrically connected to the image sensor and adapted to receive and digitally filter the digitized electronic raw image to form a digitized contrast-enhanced image.

3. The imaging system of claim 2, wherein the image processor is configured to perform frequency-space filtering using an enhanced modulation transfer function.

4. The imaging system of claim 1, further comprising an image processor electrically connected to the image sensor and adapted to receive and digitally average a number N of digitized electronic raw images to form a noise-reduced electronic raw image.

5. The imaging system of claim 1, wherein SA≦75λ.

6. The imaging system of claim 1, wherein the aperture stop is located at an axial position that substantially minimizes comatic aberration.

7. The imaging system of claim 1, wherein at least one of the lenses is made of either glass or plastic.

8. The imaging system of claim 1, wherein the negative lens element in the second group has Abbe number selected to substantially reduce or eliminate chromatic aberration.

9. The imaging system of claim 1, wherein both the first and second lens groups contribute an amount of spherical aberration.

10. The imaging system of claim 9, wherein the second lens group contributes a larger amount of spherical aberration than the first lens group.

11. The imaging system of claim 1, wherein the optical system has an F/# such that F/1.4≦F/#≦F/16.

12. The imaging system of claim 1, wherein the meniscus lens elements in the first lens group are configured to substantially compensate field aberrations in the second lens group.

13. The imaging system of claim 1, wherein the second lens group consists of said doublet lens and a most imagewise positive lens element.

14. The imaging system of claim 13, wherein the lens elements making up the doublet include adjoining planar surfaces interior to the doublet.

15. The imaging system of claim 1, wherein the most objectwise meniscus lens element has surfaces that are convex relative to the object, and wherein the most imagewise meniscus lens element has surfaces that are concave relative to the object.

* * * * *